(12) United States Patent
Wang et al.

(10) Patent No.: US 6,710,037 B2
(45) Date of Patent: Mar. 23, 2004

(54) METHOD OF TREATING ANDROGEN-DEPENDENT DISORDERS

(75) Inventors: Lynn Wang, Fanwood, NJ (US); Richard W. Bond, Union, NJ (US); Jonathan A. Pachter, Maplewood, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/137,057

(22) Filed: May 1, 2002

(65) Prior Publication Data

US 2002/0165195 A1 Nov. 7, 2002

Related U.S. Application Data

(60) Provisional application No. 60/287,756, filed on May 1, 2001.

(51) Int. Cl.$^7$ .................................................. A61K 48/00
(52) U.S. Cl. ..................... 514/44; 430/320.1; 424/94.1; 536/24.5
(58) Field of Search .................... 514/44; 430/320.1; 424/94.1, 93.1, 93.2; 536/24.1, 24.5; 435/183; 429/94.1

(56) References Cited

FOREIGN PATENT DOCUMENTS

WO      WO 00/07576     *  2/2000

OTHER PUBLICATIONS

Verma, I. M. et al. "Gene Therapy–promises, Problems and Prospects" (1997) Nature vol. 389, pp. 239–242.*
Rozenberg, Y. et al. "Alternative Gene Delivery" S.T.P. Pharma Sci (2001) vol. 11, pp. 21–30.*
Balicki, D. et al. "Gene Therapy of Human Disease" (2002) Medicine vol. 81, pp. 69–86.*
Gura. T. "Systems for Identifying New Drugs Are Often Faulty" (1997) Science vol. 273, pp. 1041–1042.*
Brothman A. R. "Cytogenetics and Molecular Genetics of Cancer of the Prostate" (2002) Am J Med Genet vol. 115, No. 3, pp. 150–156.*
Kunynetz, R. "Systemic Antibiotic Therapy for Acne: A Review" (2002) Skin Therapy Lett vol. 7, No. 5, pp. 3–7.*
Abbott, D. H. et al. "Developmental Origin of Polycyhstic Ovary Syndrome—A Hypothesis" (2002) J Endocrinol vol. 174, No. 1, pp. 1–5.*

Jin, Y. et al. "Steroid 5.alpha.–reductases and 3.alpha.–hydroxysteroid Dehydrogenases: Key Enzymes in Androgen Metabolism" (2001) Metabolism vol. 15, No. 1, pp. 79–94.*
Carducci et al., "Prostate cancer treatment strategies based on tumor–specific biological principles: Future directions," Semin. Oncol., 23(6 Suppl. 14):56–62 (1996).
Délos et al., "Testosterone metabolism in primary cultures of human prostate epithelial cells and fibroblasts," J. Steroid Biochem. Mol. Biol., 55(3–4):375–383 (1995).
Gleave et al., "Serum prostate specific antigen levels in mice bearing human prostate LNCaP tumors are determined by tumor volume and endocrine and growth factors," Cancer Res., 52(6):1598–1605 (1992).
Harrison and Glode, "Current challenges of gene therapy for prostate cancer," Oncology (Huntingt), 11(6):845–850 (1997).
Hrouda et al., "Gene therapy for prostate cancer," Semin. Oncol., 26(4):455–471 (1999).
Khanna et al., "Substrate specificity gene structure, and tissue–specific distribution of multiple human 3α–hydroxysteroid dehydrogenases," J. Biol. Chem., 270(34):20162–20168 (1995).
Neri et al., "A biological profile of a nonsteroidal antiandrogen, SCH 13521 (4'–nitro–3'trifluoromethylisobutyranilide)," Endocrinology, 91(2):427–437 (1972).
Penning et al., "Mammalian 3α–hydroxysteroid dehydrogenases," Steroids, 61(9):508–523 (1996).
Wright et al., "Relative potency of testosterone and dihydrotestosterone in preventing atrophy and apoptosis in the prostate of the castrated rat," J. Clin. Invest., 98(11):2558–2563 (1996).
Zhang and Russell, "Vectors for cancer gene therapy," Cancer Metastasis Rev., 15(3):385–401 (1996).

* cited by examiner

Primary Examiner—Dave T. Nguyen
Assistant Examiner—Jon Eric Angell
(74) Attorney, Agent, or Firm—Sandy Zaradic

(57) ABSTRACT

Novel methods of treating subjects afflicted with an androgen-dependent disorder, such as prostate cancer and benign prostatic hyperplasia are disclosed. Specifically, methods of treating androgen-dependent disorders by introducing a polypeptide or a polynucleotide encoding the polypeptide, which enhances inactivation of active androgens, are described.

13 Claims, No Drawings

METHOD OF TREATING ANDROGEN-DEPENDENT DISORDERS

REFERENCE TO RELATED APPLICATIONS

This application claims the benefit of U.S. Provisional Application Ser. No. 60/287,756 filed May 1, 2001.

All references cited herein are incorporated in their entirety by reference.

TECHNICAL FIELD OF INVENTION

The present invention relates to methods of using polypeptides or polynucleotides that encode polypeptides which enhance inactivation of active androgens for the treatment of androgen-dependent disorders. Specifically, the present invention relates to methods of treating conditions wherein androgen activity is implicated such as prostate cancer, benign prostatic hyperplasia and other androgen-dependent disorders such as androgenic alopecia.

BACKGROUND OF THE INVENTION

An androgen-dependent disorder refers to any disorder that can benefit from a decrease in androgen stimulation and includes pathological conditions that depend on androgen stimulation. An androgen-dependent disorder can result from an excessive accumulation of testosterone or other androgenic hormone; increased sensitivity of androgen receptors to androgen; or an increase in androgen-stimulated transcription. Examples of androgen-dependent disorders include prostate cancer, benign prostatic hyperplasia, acne vulgaris, seborrhea, female hirsutism, androgenic alopecia (which includes female and male pattern baldness), and polycystic ovary syndrome. Early attempts to provide a chemotherapeutic agent to counter the undesirable results of androgen-dependent disorders resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri et al., "A Biological Profile of a Nonsteroidal Antiandrogen, SCH 13521 (4'-Nitro-3'-Trifluoromethylisobutyranilide)", *Endocrinology*, 91(2):427–437 (1972). Unfortunately, even though these products are largely devoid of direct hormonal stimulatory effects, they compete with all natural androgens for receptor sites. Hence these products have a tendency to feminize a male host or the male fetus of a female host and/or initiate feedback effects that cause hyperstimulation of the testes with increased androgen production.

Growth of prostate tissue is androgen-dependent in benign prostatic hyperplasia (BPH) and early stage prostate cancer. Commonly, treatment of prostate cancer is based on surgery and/or radiation therapy, but these methods also have deleterious side effects and are ineffective in a significant percentage of cases. For example, radical prostatectomy is often accompanied by a period of dysfunction. Likewise, radiation therapy not only invokes acute adverse effects but at times also leads to long-term complications that can be debilitating or even life threatening, requiring more invasive treatments or hospitalization.

Cytotoxic chemotherapy is largely ineffective in treating prostate cancer. Even though recently developed cytotoxic agents (e.g., paclitaxel, docetaxel, and vinorelbine) have been shown to decrease prostate-specific antigen (PSA) and the pain secondary to cancer, the majority of studies using chemotherapy have failed to improve the duration of overall survival when compared to appropriate controls. Plus, the toxicity associated with these agents is unsuitable for treating elderly patients.

Luteinizing hormone-releasing hormone (LHRH) receptor agonists, and more recently antagonists, are widely used for treatment of hormone-sensitive prostate cancer. But the testicular atrophy and the loss of libido, muscle mass and erectile function that results from decreased gonadotropin levels is only tolerable for life-threatening indications. Similarly, surgical castration is an alternative for decreasing serum androgens to treat advanced prostate cancer, but the loss of function which results can only be considered for life-threatening conditions.

5α-reductase inhibitors, such as finnsteride, that inhibit reduction of testosterone to the more active androgen 5α-dihydrotestosterone (DHT) are used for the treatment of BPH. But 5α-reductase inhibitors are only marginally effective in treatment of BPH and often require at least six months of treatment before efficacy may be observed. This marginal activity may be due to prostatic accumulation of active testosterone to eight times the normal level (Wright et al., "Relative Potency of Testosterone and Dihydrotestosterone in Preventing Atrophy and Apoptosis in the Prostate of the Castrated Rat", *J. Clin. Invest.*, 98(11):2558–2563 (1996)).

An alternative approach involves gene therapy, that is, the introduction of a gene into cells for therapeutic purposes. As with more conventional therapies, the success of gene therapy relies on targeting cells selectively and effectively without adversely affecting other cells. For example, gene therapy using E-cadherin, a polypeptide involved in cell-cell and cell-matrix interactions, was proposed as a means of limiting the metastasis of cancerous cells. This approach, however, has been unsuccessful; apparently because other cadherins are also involved in the metastasis of cancerous cells. In another study, patients were treated with autologous genetically modified tumor cells that secreted granulocyte-macrophage colony-stimulating factor (GM-CSF) in an effort to elicit an immune response against prostate cancer antigens. Unfortunately, only a small fraction of these patients responded to the treatment by producing antibodies; and of those antibodies produced, none appeared to be prostate-specific.

The present inventors have responded to the above needs by developing novel approaches for the treatment of androgen-dependent disorders. In contrast to other approaches such as castration, LHRH agonists, LHRH antagonists and 5α-reductase inhibitors which focus on decreasing synthesis of active androgens to decrease androgen stimulation, the present invention focuses on enhancing inactivation of active androgens, by increasing their degradation or elimination. Surprisingly, the present invention has resulted in tumor regression in human tumor (e.g., LNCaP tumor) xenograft studies in mice, whereas approaches that decreased androgen synthesis failed to induce tumor regression in this model. Additionally, the present invention may be practiced locally thereby decreasing androgen stimulation in the target tissue and thus avoiding systemic side effects.

SUMMARY OF THE INVENTION

The present invention provides a method for treating an androgen-dependent disorder comprising administering to a patient suffering from the androgen-dependent disorder an effective amount of polypeptide or a polynucleotide encoding the polypeptide which enhances inactivation of an active androgen.

In a preferred embodiment, the androgen-dependent disorder includes but is not limited to prostate cancer, benign prostatic hyperplasia, acne vulgaris, seborrhea, female hirsutism, androgenic alopecia, and polycystic ovary syndrome.

In one preferred embodiment, the polypeptide reduces 5α-dihydroxytestosterone (DHT) to 5α-androstane-3α-17β-diol (3α-diol). In a more preferred embodiment, the polypeptide is a 3α-hydroxysteroid dehydrogenase (3α-HSD) enzyme. More preferably, the polypeptide is a 3α-HSD type 1 (3α-HSD1), a 3α-HSD type 2 (3α-HSD2), or a 3α-HSD type 3 (3α-HSD3) enzyme.

In another preferred embodiment, the polypeptide reduces 5α-dihydroxytestosterone (DHT) to 5α-androstane-3β-17β-diol (3β-diol). In a more preferred embodiment, the polypeptide is a 3β-hydroxysteroid dehydrogenase (3β-HSD) enzyme.

In yet another preferred embodiment, the polypeptide oxidizes testosterone to androst-4ene-3,17-dione or oxidizes DHT to 5α-androstane-3,17-dione (5α-dione). In a more preferred embodiment, the polypeptide is an oxidative 17β-hydroxysteroid dehydrogenase (17β-HSD) enzyme. More preferably, the polypeptide is a 17β-HSD type 2 (17β-HSD2), a 17β-HSD type 4 (17β-HSD4), or a 17β-HSD type 6 (17β-HSD6) enzyme.

In still another preferred embodiment, the polypeptide conjugates one or more glucuronide moieties to an androgen. In a more preferred embodiment, the polypeptide is an uridine diphosphoglucoronosyltransferase (UGT) enzyme. More preferably, the polypeptide is a UGT class 2 enzyme or a UGT class 2B enzyme. Still more preferably, the polypeptide is a UGT2B15, a UGT2B17 or a UGT2B20 enzyme.

In a preferred embodiment, the present invention further comprises administering an active agent.

In a preferred embodiment, the polypeptide is administered systemically, regionally or locally.

In a preferred embodiment, the polypeptide or polynucleotide is administered in a multiplicity of treatments.

In a preferred embodiment, the polynucleotide is part of an expression cassette.

In one preferred embodiment, the expression cassette comprises a prostate-specific promoter.

In another preferred embodiment, the expression cassette comprises a non-prostate-specific promoter. More preferably, the non-prostate-specific promoter is selected from the group consisting of a cytomegalovirus (CMV), a simian virus 40 (SV40), and a long-terminal repeat (LTR) promoter. In a more preferred embodiment, the expression cassette containing the non-prostate-specific promoter is administered intraprostatically.

In a preferred embodiment, the expression cassette is part of a vector. More preferably, the vector is selected from the group consisting of a recombinant adeno-associated viral vector, a recombinant adenoviral vector, a recombinant retroviral vector, a recombinant simian viral vector and a recombinant lentiviral vector.

In a preferred embodiment, the expression cassette is administered as a composition comprising viral particles, wherein the viral particles administered per treatment are in a dose ranging from about $10^9$ to about $10^{13}$.

Definitions

To aid in understanding the invention, several terms are defined below.

The term "androgen-dependent disorder" refers to any disorder that can benefit from a decrease in androgen stimulation and includes pathological conditions that depend on androgen stimulation. An "androgen-dependent disorder" can result from an excessive accumulation of testosterone or other androgenic hormone; increased sensitivity of androgen receptors to androgen; or an increase in androgen-stimulated transcription. Examples of "androgen-dependent disorders" include prostate cancer, benign prostatic hyperplasia, acne vulgaris, seborrhea, female hirsutism, androgenic alopecia (which includes female and male pattern baldness), and polycystic ovary syndrome.

The phrase "enhances inactivation" of an active androgen refers to an increase in the conversion of active androgens to inactive androgens. Alternatively, the phrase "enhances inactivation" of active androgen refers to an increase in the elimination of androgen. For example, elimination of androgen results from the conjugation of one or more glucuronide moieties to an androgen by a UGT enzyme.

The term "active androgen" refers to DHT or any other endogenous molecule with a high affinity for the androgen receptor which when bound induces transcription of androgen-dependent genes. Examples of active androgens include testosterone (Kd=0.25 nM) and DHT (Kd=0.06 nM). In contrast, the term "inactive androgen" refers to an endogenous molecule with a relatively lower affinity for the androgen receptor (Kd greater than 5 nM). Examples of inactive androgens include 3α-diol (Kd=1 μM) and androst-4-ene-3,17-dione (androstenedione) (Kd=8 nM).

The term "3α-hydroxysteroid dehydrogenase (3α-HSD)" refers to any enzyme that reduces DHT to androstane-3α-17β-diol (3α-diol). Examples of "3α-HSD" include 3α-HSD type 1 enzyme, 3α-HSD type 2 enzyme and 3α-HSD type 3 enzyme.

The term "3β-hydroxysteroid dehydrogenase (3β-HSD)" refers to any enzyme that reduces DHT to androstane-3β-17β-diol (3β-diol).

The term "17β-hydroxysteroid dehydrogenase (17β-HSD)" refers to any enzyme that oxidizes testosterone to androst-4-ene-3,17-dione (androstenedione) or that oxidizes DHT to androstane-3,17-dione. Examples of "17β-HSD" include 17β-HSD type 2 enzyme, 17β-HSD type 4 enzyme and 17β-HSD type 6 enzyme.

The term "uridine diphosphoglucuronosyltransferase (UGT)" refers to any enzyme that conjugates one or more glucuronide moieties to an androgen (e.g., testosterone and DHT) or androgen metabolite. Examples of UGT include UGT class 2 and class 2B enzymes (e.g., UGT2B15, UGT2B20, and UGT2B17).

The term "active agent" refers to any compound that decreases androgenic stimulation or that has anti-tumor activity. Examples of active agents include a P450 CYP 17 inhibitor, a 17β-HSD type 3 inhibitor, a 17β-HSD type 5 inhibitor, a LHRH agonist, a LHRH antagonist, an antiandrogen and or/other anti-tumor agents.

The term "P450 CYP 17 inhibitor" refers to any compound that decreases the conversion of progesterone to 17α-hydroxyprogesterone and/or 17α-hydroxyprogesterone to androstenedione. In addition, the term "P450 CYP 17 inhibitor" refers to any compound that decreases the conversion of pregnenolone to 17α-hydroxypregnenolone and/or 17α-hydroxypregnenolone to dihydroepiandrosterone.

The term "antiandrogen" refers to an inhibitor of the androgen receptor. Examples of antiandrogens include flutamide, bicalutamide and nilutamide.

The term "polynucleotide" refers to purine- and pyrimidine-containing polymers of any length, either polyribonucleotides or polydeoxyribonucleotides or mixed polyribo-polydeoxyribonucleotides. This includes singleand double-stranded molecules (i.e., DNA-DNA or DNA-RNA, and RNA-RNA hybrids) as well as "polypeptide polynucleotides" (PNA) formed by conjugating bases to an amino acid backbone. This also includes polynucleotides containing modified bases including those that permit correct read through by a polymerase while not altering expression of a polypeptide encoded by that polynucleotide. The term "polynucleotide" includes both the sense and antisense strands as either an individual single strand or in the context of a duplex.

The phrase "polynucleotide encoding" refers to a polynucleotide that directs the expression of a specific polypeptide. The polynucleotides include both the DNA strand sequence that is transcribed into RNA and the RNA sequence that is translated into polypeptide. The polynucleotides include both the full-length polynucleotides as well as non-full length sequences derived from the full-length sequences. It being further understood that the sequence includes the degenerate codons of the native sequence or sequences which can be introduced to provide a codon preference in a specific host cell.

A "conservative substitution", when describing a polypeptide refers to a change in the amino acid composition of the polypeptide that does not substantially alter the polypeptide's activity. Thus, "conservatively modified variations" of a particular amino acid sequence refers to amino acid substitutions of those amino acids that are not critical for polypeptide activity. Alternatively, "conservatively modified variations" refers to substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. For example, the following six groups each contain amino acids that are conservative substitutions for one another:

1) Alanine (A), Serine (S), Threonine (T);
2) Aspartic acid (D), Glutamic acid (E);
3) Asparagine (N), Glutamine (O);
4) Arginine (R), Lysine (K);
5) Isoleucine (I), Leucine (L), Methionine (M), Valine (V); and
6) Phenylalanine (F), Tyrosine (Y), Tryptophan (W).

See also, Voet and Voet, *Biochemistry*, John Wiley and Sons (1990) pp. 59–74; Creighton, *Proteins: Structure and Molecular Properties*, W. H. Freeman and Company (1984). In addition, individual substitutions, deletions or additions which alter, add or delete a single amino acid or a small percentage of amino acids in an encoded sequence are also "conservatively modified variations".

The phrase "expression cassette" refers to nucleotide sequences that are capable of affecting expression of a gene in compatible hosts. Expression cassettes include at minimum a promoter and a gene transcribed from that promoter. A transcription termination signal can also form part of the expression cassette; and additional factors necessary or helpful in effecting expression can also be used.

The term "administering" when referring to administering to a patient a polypeptide or polynucleotide encoding a polypeptide, is used herein to refer to contacting a cell with a polypeptide or polynucleotide encoding a polypeptide such that the polypeptide or polynucleotide is internalized into the cell. In this context, contacting a cell with a polynucleotide is equivalent to transferring a gene into a cell wherein the polynucleotide is maintained episomally or is integrated into the cell's genome. Where the drug is lipophilic or the polynucleotide is complexed with a lipid (e.g., a cationic lipid), simple contacting will result in transport (active, passive and/or diffusive) into the cell. Alternatively the drug and/or polynucleotide can by itself, or in combination with a carrier composition be actively transported into the cell. Thus, for example, where the polynucleotide is present in an infective vector (e.g., an adenovirus) the vector can mediate uptake of the polynucleotide into the cell. The polynucleotide can be complexed to agents that interact specifically with extracellular receptors to facilitate delivery of the polynucleotide into the cell, examples include ligand/polycation/DNA complexes as described in U.S. Pat. No. 5,166,320 (Wu et al.) and U.S. Pat. No. 5,635,383 (Wu et al.). Additionally, viral delivery can be enhanced by recombinant modification of the knob or fiber domains of the viral genome to incorporate cell targeting moieties.

The term "recombinant" refers to DNA that has been isolated from its native or endogenous source and modified either chemically or enzymatically to delete naturally occurring flanking nucleotides or provide flanking nucleotides that do not naturally occur. Flanking nucleotides are those nucleotides which are either upstream or downstream from the described sequence or sub-sequence of nucleotides.

A "vector" comprises a polynucleotide that can either transiently or stably transfect or transduce a cell such that the polynucleotide is maintained episomally or integrated within the host cell's genome. It will be recognized that a vector can be a naked polynucleotide, or a polynucleotide complexed with polypeptide or lipid. The vector optionally comprises viral or bacterial polynucleotides and/or polypeptides, and/or membranes (e.g., a cell membrane, a viral lipid envelope). It is recognized that vectors often include an expression cassette wherein the polynucleotide of interest is under the control of a promoter. Vectors include, but are not limited to replicons (e.g., plasmids, bacteriophages) to which fragments of DNA can be attached and become replicated. Vectors thus include, but are not limited to RNA and autonomous self-replicating circular DNA (plasmids). Vectors may also be of viral origin, for example, recombinant adeno-associated viral vector, recombinant adenoviral vector, recombinant retroviral vector, recombinant simian viral vector and recombinant lentiviral vector. Where a recombinant microorganism or cell culture is described as hosting an "expression vector" this includes both extrachromosomal circular DNA and DNA that has been incorporated into the host chromosome(s). Where a host cell is maintaining a vector, the vector can either be stably replicated by the cells during mitosis as an autonomous structure, or is incorporated within the host's genome.

The term "effective amount" is intended to mean the amount of polypeptide, polynucleotide encoding the polypeptide, or compound which enhances inactivation of an active androgen thereby alleviating or diminishing the symptoms or severity of the androgen-dependent disorder.

The term "viral particles" refers to intact virions. The concentration of infectious adenovirus viral particles is typically determined by spectrophotometric detection of DNA, as described, for instance, by Huyghe et al., "Purification of a Type 5 Recombinant Adenovirus Encoding Human p53 by Column Chromatography", *Hum. Gene Ther.*, 6(11):1403–1416 (1995).

The abbreviation "PN" as used herein, stands for "particle number". The particle number is the total calculated number of infectious viral particles.

The abbreviation "C.I.U." as used herein, stands for "cellular infectious units." The C.I.U. is calculated by measuring viral hexon polypeptide positive cells (e.g., 293 cells) after a 48 hr infection period (Huyghe et al., "Purification of a Type 5 Recombinant Adenovirus Encoding Human p53 by Column Chromatography", Hum. Gene Ther., 6(11): 1403–1416 (1995)).

The abbreviation "m.o.i." as used herein refers to "multiplicity of infection" and is the C.I.U. per cell.

The term "tumorigenic" or "tumorigenicity" are intended to mean having the ability to form tumors or capable of causing tumor formation.

The term "systemic administration" refers to administration of a composition (e.g., polypeptide) in a manner that results in its introduction into the circulatory system. The term "regional administration" refers to administration of a composition into a specific anatomical space, for example, intraperitoneal, intrathecal, subdural, or to a specific organ, and the like. The term "local administration" refers to administration of a composition into a limited, or circumscribed, anatomic space, for example, intratumoral injection into a tumor mass, subcutaneous injections, intramuscular injections, and the like. Any one of skill in the art would understand that local administration or regional administration can also result in entry of the composition into the circulatory system.

DETAILED DESCRIPTION OF THE INVENTION

The present invention provides new methods of treating androgen-dependent disorders by administering to a patient suffering from the androgen-dependent disorder an effective amount of a polypeptide or a polynucleotide encoding the polypeptide which enhances inactivation of an active androgen.

The androgen pathway comprises a series of steps by which cholesterol is converted into androgens. Following are examples of some of the known reactions. P450 SCC converts cholesterol to pregnenolone. Pregnenolone, in turn, may be converted to progesterone by $3\beta$-HSD. Alternatively, pregnenolone may be converted to $17\alpha$-hydroxypregnenolone by CYP 17; and $17\alpha$-hydroxypregnenolone to dihydroepiandrosterone. CYP 17 also converts progesterone to $17\alpha$-hydroxyprogesterone; and $17\alpha$-hydroxyprogesterone to androst-4-ene-3,17-dione (androstenedione). Reductive $17\beta$-HSD isoforms reduce androstenedione to testosterone. Conversely, oxidative $17\beta$-HSD isoforms oxidize testosterone to androstenedione. In addition, androstenedione can be reduced to $5\alpha$-androstane-3,17-dione by $5\alpha$-reductase; and $5\alpha$-androstane-3,17-dione can be further reduced to androsterone by $3\alpha$-HSD. Likewise, testosterone can be reduced to DHT by $5\alpha$-reductase; and DHT can be further reduced to androstane-$3\alpha$,$17\beta$-diol by $3\alpha$-reductase. Moreover, $17\beta$-HSD converts $5\alpha$-androstane-3,17-dione to/from DHT; as well as androsterone to/from androstane-$3\alpha$,$17\beta$-diol. Modulation of the androgen pathway to produce less active androgens would be desirable for the treatment of androgen-dependent disorders.

The impact of androgen-dependent disorders can be minimized by administering an amount of polypeptide or a polynucleotide encoding the polypeptide which enhances inactivation of an active androgen by converting an active androgen to an inactive androgen thus decreasing androgen-dependent transcription. In the case of prostate cancer or BPH, decreasing androgen-dependent transcription would lead to a decrease in prostatic cell hyperplasia.

In one embodiment of the invention, the polypeptide is a wild-type or modified isozyme of reductive $3\alpha$-HSD (e.g., type 1, 2, 3) which converts DHT to androstane-$3\alpha$-$17\beta$-diol. In another embodiment, the polypeptide is a wild-type or modified isozyme of oxidative $17\beta$-HSD (e.g., type 2, 4, 6), which could be used to convert testosterone back to androstenedione.

In another embodiment of the invention, a wild-type or modified isozyme of UGT (e.g., class 2, class 2B (UGT 2B15, UGT2B17, UGT2B20)) could be used to transfer glucuronide to androgens so as to enhance inactivation and elimination of androgens.

Administration of Therapeutic Polypeptide

Polypeptides may be administered locally, regionally, or systemically. In a preferred embodiment, polypeptides of the present invention are administered directly into the target tissue (e.g., intraprostatically) and in the case of prostate cancer directly at the tumor site (i.e., intratumorally). Alternatively, in a preferred embodiment, the polypeptide is combined with a pharmaceutically acceptable carrier (excipient) to form a pharmacological composition (see discussion on "Formulations" below). The polypeptide will be administered in a therapeutically effective dose in an amount sufficient to cure or at least partially arrest the disorder and/or its manifestation. Amounts effective for this use will depend upon the severity of the disorder and the general state of the patient's health.

Administration of Therapeutic Gene

The polynucleotide encoding a therapeutic polypeptide is preferably delivered to the target cells by a vector. Vectors can be of non-viral (e.g., plasmids) or viral origin (e.g., adenovirus, adeno-associated virus, retrovirus, simian virus 40, lentivirus, herpes virus, vaccinia virus). Non-viral vectors are preferably complexed with agents to facilitate the entry of the DNA across the cellular membrane. Examples of such non-viral vector complexes include formulations with polycationic agents that facilitate condensation of DNA and lipid-based delivery systems. An example of a lipid-based delivery system would include liposome based delivery of polynucleotides.

In the preferred practice of the invention, the vector is a viral vector, particularly a modified adenoviral vector. Such viral vectors have been modified by recombinant DNA technology to enable the expression of the polynucleotide in the target cell.

In a preferred embodiment, the polynucleotide vector utilizes a tissue-specific promoter to express the therapeutic gene locally in the target tissue. For example, a preferred vector for the treatment of benign prostatic hyperplasia would utilize a prostate-specific promoter to target expression of a therapeutic polypeptide to prostate cells specifically. A polynucleotide vector utilizing tissue-specific promoters could be administered systemically, regionally, or locally. Tissue-specific promoters include chimeric promoters. Chimeric promoters include polynucleotides incorporating one or more tissue-specific enhancer elements with viral promoter sequences to achieve high-level tissue-specific expression.

In another preferred embodiment, the polynucleotide vector utilizes a non-tissue-specific promoter. A polynucleotide vector utilizing a non-tissue-specific promoter to drive expression of a therapeutic polypeptide would preferably be administered regionally or locally. For example, in the treatment of prostate cancer, a vector utilizing a non-prostate-specific promoter would preferably be administered intraprostatically.

Gene Transfer

The gene used in the present invention can be introduced to the cells either as a polypeptide or as a polynucleotide.

Where the gene is provided as a polypeptide, a gene expression product (e.g., polypeptide or fragment thereof possessing androgen decreasing activity) is delivered to the target cell using standard methods for polypeptide delivery (see discussion on "Administration of therapeutic polypeptide" above). Alternatively, the gene can be introduced into the cell using conventional methods of delivering polynucleotides to cells. These methods typically involve either in vivo or ex vivo gene therapy. Particularly preferred methods of delivery include lipid or liposome delivery and/or the use of viral vectors (e.g., retroviral or adenoviral vectors).

Gene Therapy

In a more preferred embodiment, the polynucleotides (e.g., cDNA(s) encoding the therapeutic gene) are cloned into vectors that are competent to transfer the therapeutic gene into cells (e.g., human or other mammalian cells) in vitro and/or in vivo. Several approaches for introducing polynucleotides into cells in vivo, ex vivo and in vitro have been used. For a review of gene therapy procedures, see, e.g., Zhang and Russell, "Vectors for Cancer Gene Therapy", Cancer Metastasis Rev., 15(3):385–401 (1996); Anderson, "Human Gene Therapy", Science, 256(5058): 808–813 (1992); Nabel and Feigner, "Direct Gene Transfer for Immunotherapy and Immunization", Trends Biotechnol., 11 (5):211–215 (1993); Mitani and Caskey, "Delivering Therapeutic Genes—Matching Approach and Application", Trends Biotechnol., 11 (5):162–166 (1993); Mulligan, "The Basic Science of Gene Therapy", Science, 260(5110): 926–932 (1993); Dillon, "Regulating Gene Expression in Gene Therapy", Trends Biotechnol., 11 (5):167–173 (1993); Miller, "Human Gene therapy Comes of Age", Nature 357: 455–460 (1992); Kremer and Perricaudet, "Adenovirus and Adeno-Associated Virus Mediated Gene Transfer", Br. Med. Bull., 51(1) 31–44 (1995); Haddada in Current Topics in Microbiology and Immunology, Doerfler and Böhm (eds) Springer-Verlag, Heidelberg Germany (1995); and Yu et al., "Progress Towards Gene Therapy for HIV Infection", Gene Ther., 1(1):13–26 (1994).

Vectors useful in the practice of the present invention are typically derived from viral genomes. Suitable vectors include recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors can also be employed which exploit advantageous merits of each of the parent vector properties (See e.g., Feng et al., "Stable in Vivo Gene Transduction Via A Novel Adenoviral/Retroviral Chimeric Vector", Nat. Biotechnol., 15(9):866–870 (1997)). Such viral genomes can be modified by recombinant DNA techniques to include the therapeutic gene and can be engineered to be replication deficient, conditionally replicating or replication competent. In a preferred practice of the invention, the vectors are replication deficient or conditionally replicating. Preferred vectors are derived from the adenoviral, adeno-associated viral and retroviral genomes.

Conditionally replicating viral vectors are used to achieve selective expression in particular cell types while avoiding untoward broad spectrum infection. Examples of conditionally replicating vectors are described in Bischoff et al., "An Adenovirus Mutant That Replicates Selectively in p53-Deficient Human Tumor Cells", Science, 274(5286): 373–376 (1996); Pennisi, "Will a Twist of Viral Fate Lead to a New Cancer Treatment?", Science, 274(5286):342–343 (1996); Russell, "Replicating Vectors for Gene Therapy of Cancer: Risks, Limitations and Prospects", Eur. J. Cancer, 30A(8):1165–1171 (1994). Additionally, the viral genome can be modified to include inducible promoters which achieve replication or expression of the transgene only under certain conditions. Examples of inducible promoters are known in the scientific literature (See, e.g. Yoshida and Hamada, "Adenovirus-Mediated Inducible Gene Expression through Tetracycline-Controllable Transactivator with Nuclear Localization Signal", Biochem. Biophys. Res. Commun., 230(2):426–430 (1997); Iida et al., "Inducible Gene Expression by Retrovirus-Mediated Transfer of a Modified Tetracycline-Regulated System", J. Virol., 70(9): 6054–6059 (1996); Hwang et al., "A Conditional Self-inactivating Retrovirus Vector That Uses a Tetracycline-Responsive Expression System", J. Virol., 71(9):7128–7131 (1997); Lee et al., "Identification of Tumor-Specific Paclitaxel (Taxol)-Responsive Regulatory Elements in the Interleukin-8 Promoter", Mol. Cell. Biol., 17(9):5097–5105 (1997); and Dreher et al., "Cloning and Characterization of the Human Selenoprotein P Promoter", J. Biol. Chem., 272(46):29364–29371 (1997). The transgene can also be under control of a tissue-specific promoter region allowing expression of the transgene only in particular cell types. Examples of prostate-specific promoters include PSA and probassin (Steiner et al., "In Vivo Expression of Prostate-Specific Adenoviral Vectors in a Canine Model", Cancer Gene Ther., 6(5):456–464 (1999)). Alternatively the viral vector can be modified to target its expression to particular tissues (Printz et al., "Fibroblast Growth Factor 2-Retargeted Adenoviral Vectors Exhibit a Modified Biolocalization Pattern and Display Reduced Toxicity Relative to Native Adenoviral Vectors", Hum. Gene Ther., 11(1): 191–204 (2000)).

In a particularly preferred embodiment, the therapeutic gene is expressed in an adenoviral vector suitable for gene therapy. The use of adenoviral vectors in vivo, and for gene therapy, is well described in the patent and scientific literature, e.g., see, Hermens et al., "Transient Gene Transfer to Neurons and Glia: Analysis of Adenoviral Vector Performance in the CNS and PNS", J. Neurosci. Methods, 71(1): 85–98 (1997); Zeiger et al., "Adenoviral Infection of Thyroid Cells: A Rationale for Gene Therapy for Metastatic Thyroid Carcinoma", Surgery 120(6):921–925 (1996); Channon et al., "Adenoviral Gene Transfer of Nitric Oxide Synthase: High Level Expression in Human Vascular Cells", Cardiovasc Res., 32(5):962–972 (1996); Huang et al., "Gene Therapy for Hepatocellular Carcinoma: Long-Term Remission of Primary and Metastatic Tumors in Mice by Interleukin-2 Gene Therapy in Vivo", Gene Ther., 3:980–987 (1996); Zepeda and Wilson, "Neonatal Cotton Rats Do Not Exhibit Destructive Immune Responses to Adenoviral Vectors", Gene Ther. 3(11):973–979 (1996); Yang et al., "Immunology of Gene Therapy with Adenoviral Vectors in Mouse Skeletal Muscle", Hum. Mol. Genet., 5:1703–1712 (1996); Caruso et al., "Adenovirus-Mediated Interleukin-12 Gene Therapy for Metastatic Colon Carcinoma", Proc. Natl. Acad. Sci. USA, 93(21): 11302–11306 (1996); Rothmann et al., "Heart Muscle-Specific Gene Expression Using Replication Defective Recombinant Adenovirus", Gene Ther., 3(10):919–926 (1996); Haecker et al., "In Vivo Expression of Full-Length Human Dystrophin From Adenoviral Vectors Deleted of all Viral Genes", Hum. Gene Ther., 7(15):1907–1914 (1996).

Particularly preferred adenoviral vectors include a deletion of some or all of the polypeptide IX gene. In one embodiment, the adenoviral vectors include deletions of the E1a and/or E1b sequences. In a most preferred embodiment, the adenoviral construct is a vector construct (e.g., pQBI-AdCHV5).

Formulations

Pharmaceutically acceptable carriers are determined in part by the particular composition being administered, as well as by the particular method used to administer the composition. Accordingly, there are a wide variety of pharmaceutical composition formulations suitable for the present invention.

Formulations suitable for parenteral administration, for example, by intravenous, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations suitable for injection of pharmaceutical compositions comprising the active ingredient (polynucleotides encoding the therapeutic polypeptide or the therapeutic polypeptide itself) can consist of: (a) liquid solutions, for example, an effective amount of the active ingredient suspended in diluents, (e.g., water, saline, or PEG 400); and (b) suitable emulsions. Formulations of the invention as injection solutions and suspensions can be prepared from sterile powders, granules, and tablets. In addition to the active ingredient, tablet forms can include one or more of the following: lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, dyes, disintegrating agents, and pharmaceutically compatible carriers.

Formulations of the invention using polynucleotides can be packaged in unit-dose or multi-dose sealed containers, (e.g., ampules and vials).

The exact composition of the formulation, the concentration of the reagents and polynucleotide in the formulation, its pH, buffers, and other parameters will vary depending on the mode and site of administration (e.g., whether systemic, regional or local administration) as well as needs related to storage, handling, shipping, and shelf life of the particular pharmaceutical composition. Parameters can be optimized depending on the particular formulation needed using routine methods and any of a number of ingredients and parameters known for injectable formulations can be used.

The dose administered to a patient, in the context of the present invention, should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of vector to be administered in treatment, the physician evaluates circulating plasma levels of the vector, vector toxicity, progression of the disease, and the production of anti-vector antibodies. The typical dose for a polynucleotide is highly dependent on route of administration and gene delivery system. Depending on delivery method the dosage can easily range from about 1 µg to 100 mg or more. In general, the dose equivalent of a naked polynucleotide from a vector is from about 1 µg to 100 µg for a typical 70 kilogram patient, and doses of vectors which include a viral particle are calculated to yield an equivalent amount of therapeutic polynucleotide.

For administration, transduced cells of the present invention can be administered at a rate determined by the $LD_{50}$ of the vector, or transduced cell type, and the side-effects of the vector or cell type at various concentrations, as applied to the mass and overall health of the patient. Administration can be accomplished via single or divided doses as described below.

In a preferred embodiment, prior to infusion, blood samples are obtained and saved for analysis. Vital signs and oxygen saturation by pulse oximetry are closely monitored. Blood samples are preferably obtained 5 minutes and 1 hour following infusion and saved for subsequent analysis. In ex vivo therapy, leukopheresis, transduction and reinfusion can be repeated, e.g., every 2 to 3 months. After the first treatment, infusions can be performed on a outpatient basis at the discretion of the clinician. If the reinfusion is given as an outpatient, the participant is monitored for at least 4, and preferably 8 hours following the therapy.

As described above, the adenoviral constructs can be administered systemically (e.g., intravenously), regionally (e.g., intraperitoneally) or locally (e.g., intraprostaticlly). Typically such administration is in an aqueous pharmacologically acceptable buffer as described above. However, in other embodiments, the adenoviral constructs or the expression cassettes are administered in a lipid formulation, more particularly either complexed with liposomes to for lipid/polynucleotide complexes or encapsulated in liposomes, more preferably in immunoliposomes directed to specific tumor markers. It will be appreciated that such lipid formulations can also be administered topically, or systemically.

Dosage

The polypeptide or polynucleotide can be administered in a single dose or a multiplicity of treatments.

In a preferred embodiment, the polynucleotide encoding polypeptide is delivered by a recombinant adenoviral vector administered in a total dose ranging from about $10^9$ to about $10^{12}$ adenovirus particles.

Routes of Delivery

Pharmaceutical compositions can be delivered by any means known in the art, e.g., systemically, regionally, or locally; by intra-arterial, intratumoral, intravenous (i.v.), parenteral, topical or local administration, as subcutaneous, intratumoral (e.g., transdermal application or local injection). Particularly preferred modes of administration include intraprostatic or intratumoral injections, especially when it is desired to have a "regional effect," e.g., to focus on a specific organ (e.g., prostate).

Treatment Regimens

Pharmaceutical compositions can be administered in a variety of unit dosage forms depending upon the method of administration. Detailed information for preparing pharmaceutical compositions can be found in such publications as Remington's Pharmaceutical Science, 15th ed., Mack Publishing Company, Easton, Pa.

In therapeutic applications, compositions containing the active ingredient are administered to a patient suffering from a disease characterized by cancer or hyperproliferation of one or more cell types in an amount sufficient to cure or at least partially arrest the disease and/or its complications. An amount adequate to accomplish this is defined as a "therapeutically effective dose" and will depend upon the severity of the disease as well as the general state of the patient's health.

Single or multiple administrations of the compositions can be administered depending on the dosage and frequency as required and tolerated by the patient. In any event, the composition should provide a sufficient quantity of the active ingredient of the present invention to effectively treat the patient. The treatment preferably results in a decrease in the manifestation of the androgen-dependent disorder.

Modifications of Therapeutic Polypeptide or Polynucleotides

One of skill in the art will appreciate that many conservative variations of the polypeptide or polynucleotides described herein yield functionally identical products. For example, due to the degeneracy of the genetic code, "silent substitutions" (i.e., substitutions of a polynucleotide which do not result in an alteration in an encoded polypeptide) are an implied feature of every polynucleotide which encodes an amino acid. Similarly, "conservative amino acid substitutions," in one or a few amino acids in an amino acid sequence are substituted with different amino acids with highly similar properties (see, the definitions section, supra), are also readily identified as being highly similar to a disclosed amino acid sequence, or to a disclosed polynucleotide which encodes an amino acid. Such conservatively substituted variations of each explicitly described sequence are a feature of the present invention.

One of skill would recognize that modifications can be made to the polypeptide without diminishing its biological activity. Some modifications can be made to facilitate the cloning, expression, or incorporation of the targeting molecule into a fusion polypeptide. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Modifications to polynucleotides and polypeptides can be evaluated by routine screening techniques in suitable assays for the desired characteristic. For instance, changes in the immunological character of a polypeptide can be detected by an appropriate immunological assay. Modifications of other properties, for example, polynucleotide hybridization to a target polynucleotide, redox or thermal stability of a polypeptide, hydrophobicity, susceptibility to proteolysis, or the tendency to aggregate are all assayed according to standard techniques.

In vitro and in vivo studies were performed on LNCaP cells, a cell line established from a metastatic lesion of human prostatic adenocarcinoma that is androgen responsive (Horoszewicz et al., *Prog. Clin. Biol. Res.*, 37:115–132 (1980)).

Example 1 describes in vitro studies regarding the conversion of androgens by 3α-HSD types 1 and 3 as well as 17β-HSD type 2. In addition, the rate of DHT conversion by 3α-HSD isozymes was explored as well as the impact of 3α-HSD on the production of PSA.

EXAMPLE 1

In vitro Studies of Androgen Conversion by 3α-HSD and 17β-HSD

LNCaP cells were transduced with recombinant adenovirus (rAdv) rAdv-3α-HSD1 (rAdvHSD1) or rAdv-3α-HSD3 (rAdv-HSD3) and then tested for their ability to convert $^{14}$C-labeled DHT to 3α-diol or $^{3}$H-labeled 3α-diol to DHT indicating predominantly reductive activities of these 3α-HSD isoforms. Both enzymes 3α-HSD1 and 3α-HSD3 catalyzed the reductive conversion of DHT to 3α-diol. In contrast, there was no detectable conversion of 3α-diol to DHT. Although there can be differences in expression levels, it appears that 3α-HSD1 was much more active than 3α-HSD3 in conversion of DHT to 3α-diol. Therefore 3α-HSD1 was chosen for proof-of-principle studies.

Androgen conversion by 17β-HSD type 2 was also examined in vitro. In brief, high-expressing 17β-HSD type 2 cell lines were established from which cellular extracts were isolated and incubated with radioactively labeled androgens to determine whether androgen conversion occurred. More specifically, human embryonic kidney (HEK) 293 cells were transfected with a DNA construct containing human 17β-HSD2 downstream of a CMV promoter and a neomycin resistance gene downstream of an SV40 promoter (pcDNA3-Invitrogen). Cell lines permanently expressing human 17β-HSD2 were selected with 650 μg/ml G418 and verified by both PCR as well as 17β-HSD2 activity assays. A high-expressing cell line of 17β-HSD2 was selected to examine androgen conversion. The high-expressing cell line was grown to about 80% confluence prior to harvesting cells by trypsinization and subsequent centrifugation. The cell pellet was then resuspended in 20 mM phosphate buffer with protease inhibitors, 1 mM EDTA, 0.25 M sucrose, and 20% glycerol. The isolated cells were lysed by sonication and centrifuged at 10,000×g to remove cellular debris. The soluble fraction was then centrifuged at 100,000×g after which the insoluble fraction was resuspended in the same buffer as above and the polypeptide content measured (Bio-Rad polypeptide assay kit). Various amounts of polypeptide were incubated with 100 nM of either $^{14}$C-androstenedione (A) under reducing conditions (NADH and NADPH) or $^{14}$C-testosterone (T) under oxidizing conditions (NAD$^+$ and NADP$^+$) for 30 minutes at 37° C. Following incubation, the resulting products were separated by thin layer chromatography (TLC) with chloroform:ethyl acetate (3:1) and the $^{3}$H-containing compounds quantitated using a phosphorimager. The data demonstrated that human 17β-HSD2 is much more active in oxidizing T to A (about 90% conversion at 1 mg) than in reducing A to T (barely detectable activity at 1 mg). Therefore, 17β-HSD2 is also a viable candidate for treating androgen-dependent disorders.

For proof-of-principle studies, 3αHSD1 was chosen. The rate of conversion of DHT to 3α-diol by 3αHSD1 was found to be dose-dependent. The rate of conversion of DHT to 3α-diol was determined as follows: 5×10$^5$ LNCaP cells were plated per well of a 6-well tissue culture plate; 48 hrs after cells were plated, rAdvHSD1 or control-Adv was added to cells; labeled DHT was added at various specified intervals of time; cells were subsequently incubated for 1 hr at 37° C. after which supernatant was collected from the individual culture dishes and collected supernatants were extracted using a mixture of chloroform:methanol followed by thin layer chromatography (TLC) to separate the labeled steroids. Based on measurements from TLC plates, the percent conversion of DHT to 3α-diol was calculated.

LNCaP cells transduced with rAdvHSD1 were assayed for production of PSA, a marker of prostate cancer and BPH aggressiveness that is dependent on androgen stimulation in LNCaP cells. PSA production was found to decrease in a dose-dependent manner after transduction with rAdvHSD1. In contrast, transduction with control virus had no effect on PSA production.

The effect of rAdvHSD1 on PSA production was further examined using R1881, a non-hydrolyzable androgen, to stimulate PSA production. In sum, rAdvHSD1 had no effect on PSA production induced by R1881 thereby supporting the hypothesis that the effect of rAdvHSD1 is mediated by enhanced conversion of DHT.

Next, in vivo studies were undertaken to examine whether the results observed in vitro were indicative of decreased androgen-dependence in vivo.

Example 2 describes in vivo studies regarding the effect on tumor growth by 3α-HSD1. Specifically, LNCaP cells transduced with rAdvHSD1 at different m.o.i. were implanted into SCID mice. In another study, established LNCaP tumors were intratumorally injected with rAdvHSD1 and harvested 21 days later to assay 3α-HSD activity.

EXAMPLE 2

In vivo Studies of Tumor Growth Using LNCaP Cells Transduced With rAdvHSD1

To test the ability of rAdvHSD1 to inhibit the growth of LNCaP tumors in SCID mice, LNCaP cells were transduced with rAdvHSD1, control-Adv, or mock transduced with PBS in vitro. After 24 hrs, the cells were washed and subcutaneously injected along with matrigel into SCID mice. LNCaP cells transduced with rAdvHSD1 and injected into SCID mice demonstrated decreased tumorigenicity in vivo. In fact, rAdvHSD1 was able to completely inhibit tumor growth in a dose-dependent manner while control-Adv had little or no effect on tumor growth. The ability of rAdvHSD1 to block growth of LNCaP cells in vivo 60 days after transduction was surprising as rAdv expression of transgenes is usually transient in vivo.

Lastly, to test the ability of rAdvHSD1 to inhibit the growth of established LNCaP tumors, LNCaP tumors were injected intratumorally with rAdvHSD1, control-Adv, or PBS. Injections started 34 days after implanting LNCaP cells subcutaneously and were delivered three times with 48 hour intervals between each injection. Intratumoral injection of rAdvHSD1 resulted in regression of LNCaP tumors in a dose-dependent manner whereas control virus had little or no effect. This dramatic tumor regression was extremely surprising, since even the dramatic decrease in serum androgens that follows surgical castration has been unable to induce regression of LNCaP tumors (Gleave et al., "Serum Prostate Specific Antigen Levels in Mice Bearing Human Prostate LNCaP Tumors Are Determined by Tumor Volume and Endocrine and Growth Factors" Cancer Res, 52(6): 1598–1605 (1992)).

To test for active transgene expression in tumors that had been intratumorally injected, tumors were harvested 21 days after the last injection with rAdvHSD1 or control-Adv and examined for 3α-HSD activity. Even after 21 days post-transduction in vivo the harvested rAdvHSD1 treated tumor cells still had high levels of 3α-HSD activity.

The above-described examples show that gene therapy which enhances inactivation of an active androgen is effective to treat androgen-dependent disorders. In the model of prostate cancer examined, 3α-HSD1 was able to decrease the level of active androgen available thereby decreasing androgen-dependent transcription and androgen-dependent tumor growth.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A method for inhibiting the activity of 5α-dihydrotestosterone (5α-DHT) in a cell, wherein the cell is present in a patient suffering from an androgen-dependent disorder, comprising directly administering into said cell of the patient suffering from the androgen-dependent disorder a replication deficient adenoviral vector that expresses a 3α-hydroxysteroid dehydrogenase (3α-HSD) enzyme.

2. The method of claim 1 wherein the androgen-dependent disorder is selected from the group consisting of prostate cancer, benign prostatic hyperplasia, acne vulgaris, seborrhea, female hirsutism, androgenic alopecia, and polycystic ovary syndrome.

3. The method of claim 1 wherein the 3α-HSD enzyme is selected from the group consisting of a 3α-HSD type 1 enzyme, a 3α-HSD type 2 enzyme, and a 3α-HSD type 3 enzyme.

4. The method of claim 1 further comprising administering a 5α-reductase inhibitor, a P450 CYP 17 inhibitor, a 17β-HSD type 3 inhibitor, a 17β-HSD type 5 inhibitor, a LHRH agonist, a LHRH antagonist, an antiandrogen, or an anti-tumor agent.

5. The method of claim 1 wherein the replication deficient adenoviral vector is administered in a multiplicity of treatments.

6. The method of claim 1 wherein the replication deficient adenoviral vector comprises a prostate-specific promoter.

7. The method of claim 1 wherein the replication deficient adenoviral vector comprises a non-prostate-specific promoter.

8. The method of claim 7 wherein the non-prostate-specific promoter is selected from the group consisting of a cytomegalovirus (CMV), a simian virus 40 (SV40), and a long-terminal repeat (LTR) promoter.

9. The method of claim 1 wherein the replication deficient adenoviral vector is administered as a composition comprising said replication deficient adenoviral particles.

10. The method of claim 1 wherein the 3α-HSD enzyme predominantly reduces 5α-dihydrotestosterone to 5α-androstane-3α-17β-diol.

11. The method of claim 1 wherein said androgen-dependent disorder is a prostate tumor and said administering is intratumoral.

12. The method of claim 1 wherein said androgen-dependent disorder is benign prostatic hyperplasia and said administering is intraprostatic.

13. The method of claim 9, wherein the replication deficient adenoviral particles administered per treatment are in a dose ranging from about $10^9$ to about $10^{13}$.

* * * * *